US010675002B2

(12) United States Patent
Mahmoud et al.

(10) Patent No.: US 10,675,002 B2
(45) Date of Patent: Jun. 9, 2020

(54) METHOD AND APPARATUS TO MEASURE TISSUE DISPLACEMENT AND STRAIN

(71) Applicants: Ahmed M Ehab Mahmoud, Giza (EG); Mohamed Tarek Mohamed Ali, Cairo (EG)

(72) Inventors: Ahmed M Ehab Mahmoud, Giza (EG); Mohamed Tarek Mohamed Ali, Cairo (EG)

(73) Assignees: Ahmed M Ehab Mahmoud, Giza (EG); Mohamed Tarek Mohamed Ali, Cairo (EG)

( * ) Notice: Subject to any disclaimer, the term of this patent is extended or adjusted under 35 U.S.C. 154(b) by 453 days.

(21) Appl. No.: 15/396,699

(22) Filed: Jan. 2, 2017

(65) Prior Publication Data

US 2018/0132830 A1  May 17, 2018

Related U.S. Application Data

(60) Provisional application No. 62/274,265, filed on Jan. 2, 2016.

(51) Int. Cl.
*A61B 8/00* (2006.01)
*A61B 8/08* (2006.01)
(Continued)

(52) U.S. Cl.
CPC ............ *A61B 8/485* (2013.01); *A61B 5/0059* (2013.01); *A61B 6/4258* (2013.01);
(Continued)

(58) Field of Classification Search
CPC ..... A61B 8/485; A61B 8/5223; A61B 5/0048; G01R 33/56358
See application file for complete search history.

(56) References Cited

U.S. PATENT DOCUMENTS 8,503,714 B2  8/2013  Park et al.
9,275,471 B2  3/2016  Hamilton
(Continued)

OTHER PUBLICATIONS

Lili Niu et al., "A Texture Matching Method Considering Geometric Transformations in Noninvasive Ultrasonic Measurement of Arterial Elasticity", Ultrasound in Med. & Biol., vol. 38, No. 3, pp. 524-533, 2012.
(Continued)

*Primary Examiner* — Eric D. Bertram
(74) *Attorney, Agent, or Firm* — Leason Ellis LLP

(57) ABSTRACT

A method for reconstructing displacement and strain maps of human tissue of a subject in vivo or other objects includes applying a mechanical deformation for a target area, imaging tissues while deformation is applied on the target area, measuring the axial and lateral displacements and axial, lateral, and shear strains of tissue in the target area, differentiating between tissues of different stiffness and strain responses, and labeling tissues of different stiffness and strain responses. In some embodiments, displacement and strain imaging are performed using a high-resolution, high-speed, highly-accuracy hierarchy recursive displacement tracking from conventional ultrasound brightness mode images. Particularly, this invention relates to the reconstruction of displacement and strain images from conventional ultrasound B-mode images acquired using any ultrasound machine of different manufacturers without the need to use carrier signals.

22 Claims, 7 Drawing Sheets

(51) Int. Cl.
*A61B 6/00* (2006.01)
*A61B 5/00* (2006.01)
*G01R 33/563* (2006.01)
*A61B 5/055* (2006.01)

(52) U.S. Cl.
CPC ............ *A61B 8/5223* (2013.01); *A61B 8/565* (2013.01); *A61B 5/0048* (2013.01); *A61B 5/0077* (2013.01); *A61B 5/055* (2013.01); *G01R 33/56358* (2013.01)

(56) References Cited

U.S. PATENT DOCUMENTS

| | | | | |
|---|---|---|---|---|
| 2009/0247871 | A1* | 10/2009 | Varghese | A61B 8/08 600/438 |
| 2014/0094702 | A1* | 4/2014 | Kim | G01N 29/0654 600/438 |
| 2015/0201905 | A1* | 7/2015 | Ivancevich | G01S 7/52042 600/438 |

OTHER PUBLICATIONS

Hyock-Ju Kwon et al., "Low-cost quasi-real-time elastography using B-mode ultrasound images", Bio-Medical Materials and Engineering 24, pp. 1673-1692, 2014.
Hirad Karimi et al., "A real-time method for breast cancer diagnosis using optical flow", The International Society for Optical Engineering, 2009.
Hao Chen et al., "Improvement of Elastographic Displacement Estimation Using a Two Step Cross-Correlation Method", Ultrasound Med Biol., pp. 48-56, 2007.
E. Yeom et al., "Improvement of ultrasound speckle image velocimetry using image enhancement techniques," Ultrasonics, vol. 54, No. 1, pp. 205-216, Jan. 2014.
Toufik Zakria et al., "Optical-Flow-Based B-Mode Elastography: Application in the Hypertensive Rat Carotid", IEEE Transactions on Medical Imaging, vol. 29, No. 2, pp. 570-578, 2010.
Lili Niu et al., "Ultrasonic particle image velocimetry for improved flow gradient imaging: algorithms, methodology and validation", Physics in Medicine and Biology., vol. 55, pp. 2103-2120, 2010.

* cited by examiner

FIG. 5
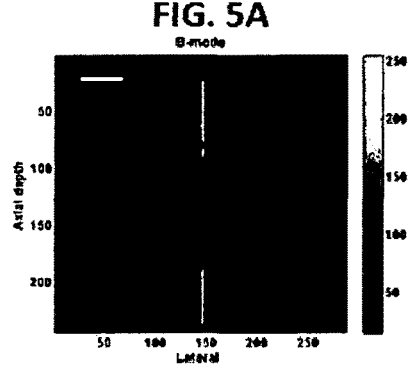
FIG. 5A
B-mode
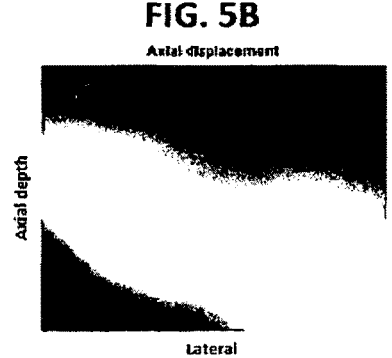
FIG. 5B
Axial displacement
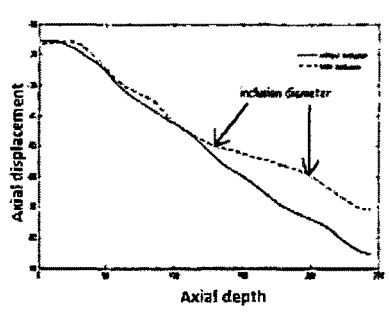
FIG. 5C
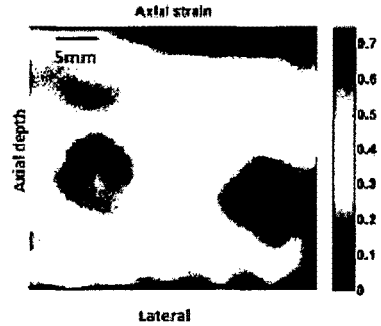
FIG. 5D
Axial strain
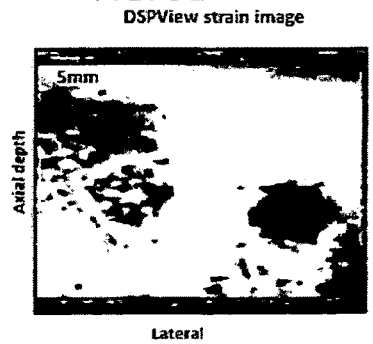
FIG. 5E
DSPView strain image

FIG. 6
FIG. 6A
Bmode
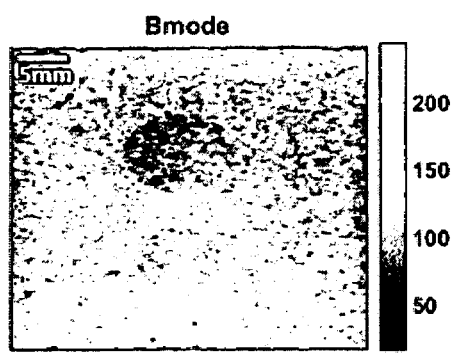
FIG. 6B
Axial displacement
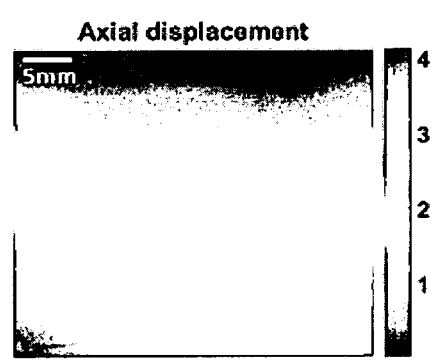
FIG. 6C
Axial strain
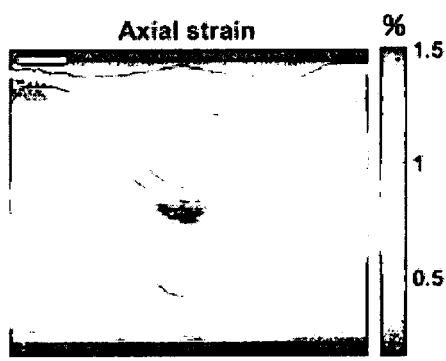
FIG. 6D
Superimposed
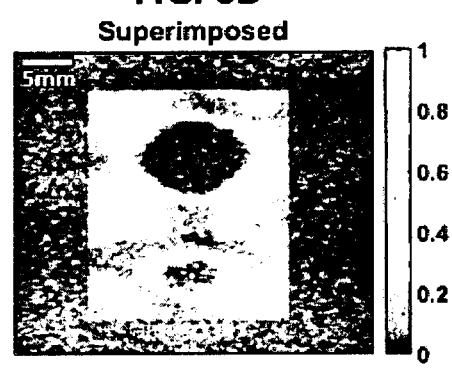

FIG. 7
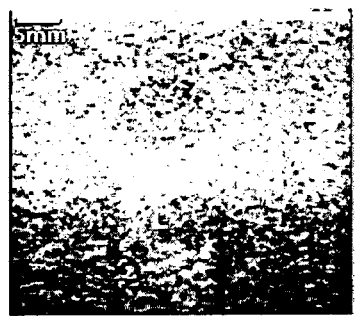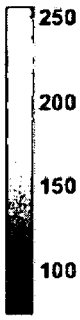
FIG. 7A
Bmode
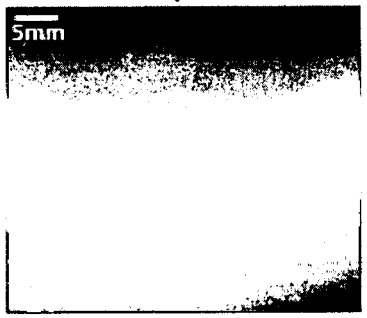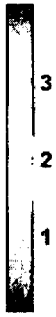
FIG. 7B
Axial displacement
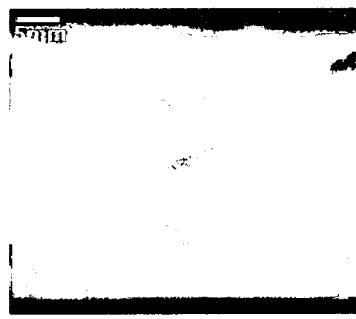
FIG. 7C
Axial strain
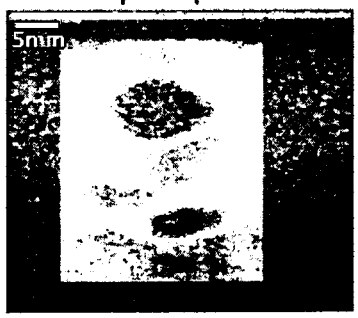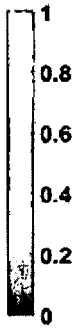
FIG. 7D
Superimposed

METHOD AND APPARATUS TO MEASURE TISSUE DISPLACEMENT AND STRAIN

CROSS-REFERENCE TO RELATED APPLICATIONS

This application claims the benefit of U.S. Provisional Application No. 62/274,265, which was filed on Jan. 2, 2016.

FIELD OF THE INVENTION

This invention relates to a method and system for the reconstruction of displacement and strain images from conventional ultrasound brightness mode (B-mode) images. Particularly, this invention relates to the reconstruction of displacement and strain images from conventional ultrasound B-mode images acquired using any ultrasound machine of different manufacturers without the need to use carrier signals. More particularly, the invention relates to a manufacturer-independent method and system for the acquisition of conventional ultrasound B-mode images from ultrasound machines and the generation of displacement and strain images from those images. Specifically, the invention relates to a constrained recursive motion tracking technique with a feature extraction algorithm that ensures a real-time high quality displacement and strain images from conventional ultrasound B-mode images acquired directly from ultrasound machines, transferred via data storage devices either optical devices (CD or DVD), hard drives, floppy drives, or any suitable device, or sent remotely via the internet or network via DICOM, Ethernet card, Bluetooth or WI-FI. The processing can be done either on personal computer, servers, clouds or any device having a processing unit and the results can be sent back to users via any of the transferring devices mentioned before to their smart phones, e-mails, website or any reachable media viewer. The invention is also further applicable to generate displacement and strain images using images acquired by other modalities such as magnetic resonance, nuclear medicine, x-ray and optical imaging methods for medical and non-medical applications to track the motion and measure strain tensors of any material.

BACKGROUND OF THE INVENTION

Ultrasound brightness mode (B-mode) noninvasive imaging is commonly used in various healthcare facilities including hospitals, medical centers, and clinics. Ultrasound B-mode provides mainly information about the anatomy of human body organs and tissue motion that can be used for medical screening and diagnosis. B-mode gray scale ultrasound images is considered the first choice when diagnosing many diseases due to its safety, high-resolution, mobility, and cost-effectiveness compared to other imaging modalities such as computed tomography (CT) and magnetic resonance imaging (MRI). However, conventional ultrasound B-mode does not provide information about the mechanical characteristics, or stiffness, of tissue that is essential for diagnosing several diseases including liver disease, atherosclerosis, and tumors. Ultrasound elastography is an emerging technology that has been used to interrogate the mechanical characteristics of soft tissues via measuring tissue strain and elasticity to describe their hardness or stiffness. Although some ultrasound companies have developed this new mode (elastography) on few of their premium and high-end ultrasound machines, this imaging mode is still not available on most ultrasound machines and ultrasound machines developed before year 2003.

This elastography mode is only compatible with these specific machines and cannot be used on other machines from the same manufacturer, i.e. until now it is a machine dependent mode and there is not machine independent elastography processing unit. Additionally, the output of elastography imaging varies from an ultrasound manufacturer to another one due to different algorithms and platforms. Both low- to medium-end and old machines do not provide access to raw radiofrequency (RF) ultrasound signals that is commonly used to reconstruct elastography in all machines. On the other hand, B-mode images are available on any commercial ultrasound machine and can be extracted via the digital video interface (DVI), high-definition multimedia interface (HDMI), video graphics adapter (VGA), S-Video, composite video out, BNC, or the universal serial bus (USB) port. Additionally, B-mode images can be sent or transferred by any data storage device like disks, or via the internet or other networks.

It is an object of the present invention to provide a method and a system for generating displacement and strain images. It is also an object of the present invention to provide a manufacturer-independent method and a system that can be used with any ultrasound machine for reconstructing displacement and strain images. Another object of this invention is to provide a commercially practicable, remote, and flexible system generating displacement and strain images from conventional B-mode ultrasound images using a machine learning algorithm to ensure the quality of the estimated Elastogram at real-time. Conventional B-mode ultrasound images acquired by any ultrasound machine, particularly those that do not have this capability. A specific object of the invention is to provide a flexible, standard and cost-effective method for generating displacement and strain images from B-mode images, cine-loop and videos acquired directly from ultrasound machines via Digital Video Interface (DVI), High-Definition Multimedia Interface (HDMI), video graphics adapter (VGA), S-Video, composite video out, BNC, or the universal serial bus (USB) or indirectly transferred through the Ethernet, WI-FI, or other data exchange or storage methods and send back the results through any of the previously mentioned ways to any internet connected device with media viewer, e-mails or a website (server) to show results. A further object of the present invention is to provide a system and technique that is computationally and time efficient, safe, standard, cost-effective and accurate for reconstructing displacement and strain images from conventional gray scale images acquired by different machines and enables the digital archiving and electronic transfer of data from machines. These and other objects of the invention will be apparent to those skilled in the art from the description that follows.

SUMMARY OF THE INVENTION

The method and the system of this invention center around the innovative concept of providing flexible, standard, manufacturer-independent, cost-effective and accurate means for displacement and strain image reconstruction for tissues or other materials in response to a mechanical, thermal, and/or other stimulation. Conventional gray scale ultrasound B-mode images can be acquired directly via the system and/or can be processed using the method described here. Image sequences acquired during stimulus can be acquired directly from machines via the DVI, HDMI, VGA, S-Video, composite video out, BNC, USB, or other output ports or transferred through the Ethernet, WI-FI, or other data storage and exchange methods. Images can be transferred remotely via the internet. Images are then fed into a computationally efficient method to measure displacements. This novel method relies on block matching of subsequent images using hierarchy recursive displacement tracking (HR-DT), with several constraints for the searching method based on physical assumptions to ensure the low computation complexity that take this algorithm to the real-time implementation and with a machine learning technique that ensures the high quality of the estimated Elastogram. A minimum of 2 levels HR-DT is used where larger kernels and search windows are used in the 1st level to estimate preliminary displacement fields with high SNR and low resolution producing coarse estimation to the displacement fields with coarse strain images. In the 2nd level, a smaller template and search windows are used to increase the resolution of estimated displacements using the priori information of level-1 HR-DT to estimate finer displacement fields and thus, high resolution and accurate strain image. Similar process will be sued in the 3rd or subsequent levels of HR-DT, if needed. A HR-DT with only 1 level is applied on few frames to determine the required skipping factor in order to produce high SNR and CNR strain images with strain range that ensures a high quality Elastogram either in the linear or nonlinear range. To enhance SNR and CNR of the output strain image, we apply a frame selection criteria that was based on observations and some physical assumptions related to Poisson ratio and how should lateral motion relate to axial motion at ideal axial stress and other assumptions that make us pick those frames that already contains enough strain to show contrast between different tissue or objects and this is only an opening for any skilled in art to expand the idea more and apply more physical constraints according to the applications. We have used WEKA [9] software for data mining and those skilled in the art can use other data mining stuff that helps them to select features or build their own. To overcome computational complexity, hierarchical constraint and axial and lateral, continuity constrains were applied in all levels of HR-DT. Although, these 3 constraints are based on physical assumptions of tissue motion like the smoothness of motion, moving at the same direction of the applied stress and the lateral motion should be much less than the axial one, we still believe that skilled in art can apply more to speed the algorithm up based on physical constraints or experiment based constraints. Strain is then evaluated as the spatial gradient of displacement maps.

In some embodiments, the system and method be integrated with any ultrasound machine regardless the manufacturer and reconstruct displacement and strain images from standard B-mode imaging sequences.

In other embodiments, the method can be applied to imaging sequences acquired from ultrasound, magnetic resonance imaging, x-ray and optical methods, PET/SPECT, OCT, and directly processed, transferred, or sent remotely from other locations via the internet or other wired or wireless data transfer protocol.

The method of this invention is particularly suited for reconstructing the displacement and strain images of objects in response to stimulation using ultrasound imaging; however the method is also suited for imaging using magnetic resonance imaging, optical and laser imaging methods, etc.

The foregoing and other objects, features, and advantages of the invention will become more apparent from the following detailed description, which proceeds with reference to the accompanying figures.

BRIEF DESCRIPTION OF THE DRAWINGS

A clear understanding of the key features of the invention summarized above may be had by reference to the appended drawings, which illustrate the method and system of the invention, although it will be understood that such drawings depict preferred embodiments of the invention and, therefore, are not to be considered as limiting its scope with regard to other embodiments which the invention is capable of contemplating. Accordingly:

FIGS. 5A-5E illustrates (A) is a B-mode gray scale ultrasound image of breast phantom including 2 masses with a dashed line passing through the inclusion (red) and solid line on background material (blue), (B) axial displacement image estimated by HR-DT, (C) graph showing gradient of axial displacement along axial depth at the two lines (red and blue) shown (A), (D) axial strain by the HR-DT technique, and (E) axial strain by DSPview code [2] that used RF signals. Both (D) and (E) show the two masses in low strain values (blue). Ultrasound B-mode images were acquired using the Sonix RP machine by Ultrasonix (Canada).

FIGS. 6A-6D illustrates (A) B-mode gray scale ultrasound image of breast phantom including 2 masses B-mode, (B) axial displacement map, (C) axial strain map, (D) superimposed pseudo-strain image. Ultrasound B-mode images were acquired using Acuson machine by Siemens (Germany).

FIGS. 7A-7D illustrates (A) B-mode gray scale ultrasound image of breast phantom including 2 masses B-mode, (B) axial displacement map, (C) axial strain map, (D) superimposed pseudo-strain image. Ultrasound B-mode images were acquired using Digison machine by IBE (Egypt).

DETAILED DESCRIPTION OF THE INVENTION

Figure 1:
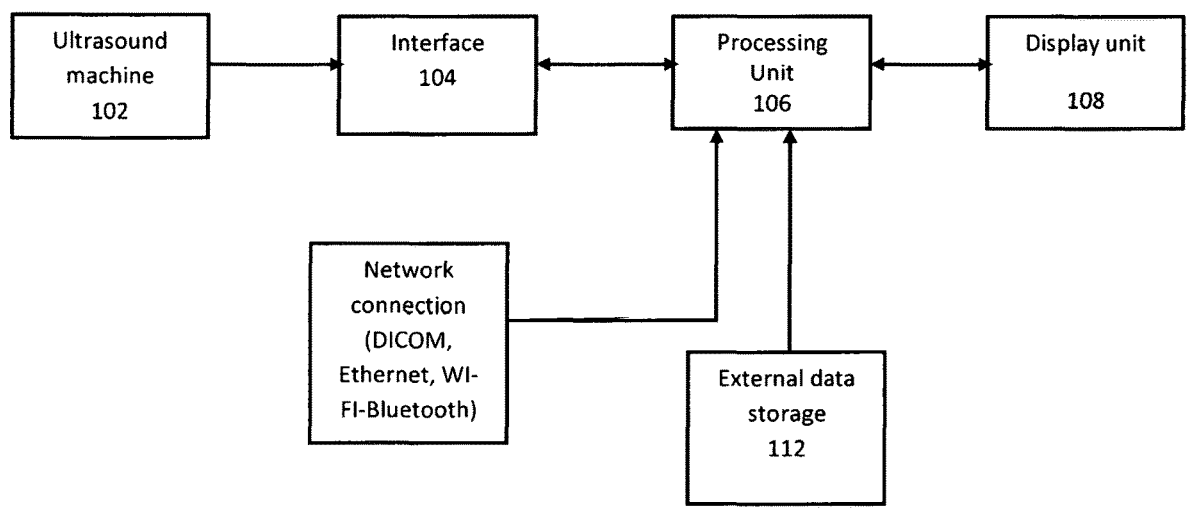
FIG. 1 is an illustration of the system schematic of the ultrasound elastography add-on module system for providing non-invasive displacement and strain measurements.

Referring to FIG. 1 images are captured from the ultrasound machine (102) using a hardware interface (104) such as video capture device then they are processed by our method in the processing unit (106) where displacements and strains between different frames are measured and displayed on the display unit (108). Images can be transferred to the processing unit by means of network connections (110) through Ethernet or WI-FI and/or external data storage (112).

Figure 2:
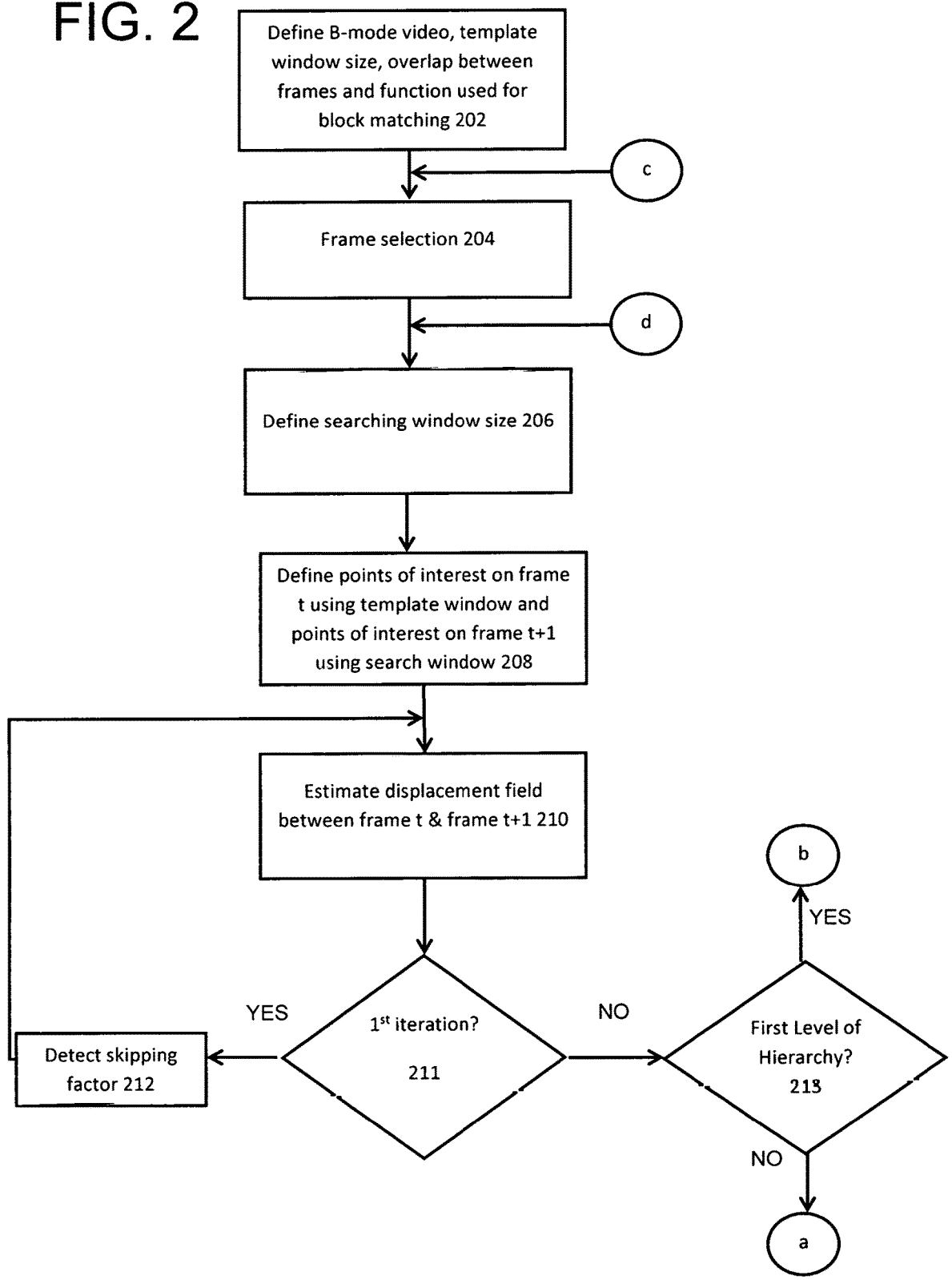
FIG. 2 is an illustration of the first part of the displacement estimation algorithm starting from acquiring the ultrasound images to initial displacement values and determining skipping frames factor.
Figure 3:
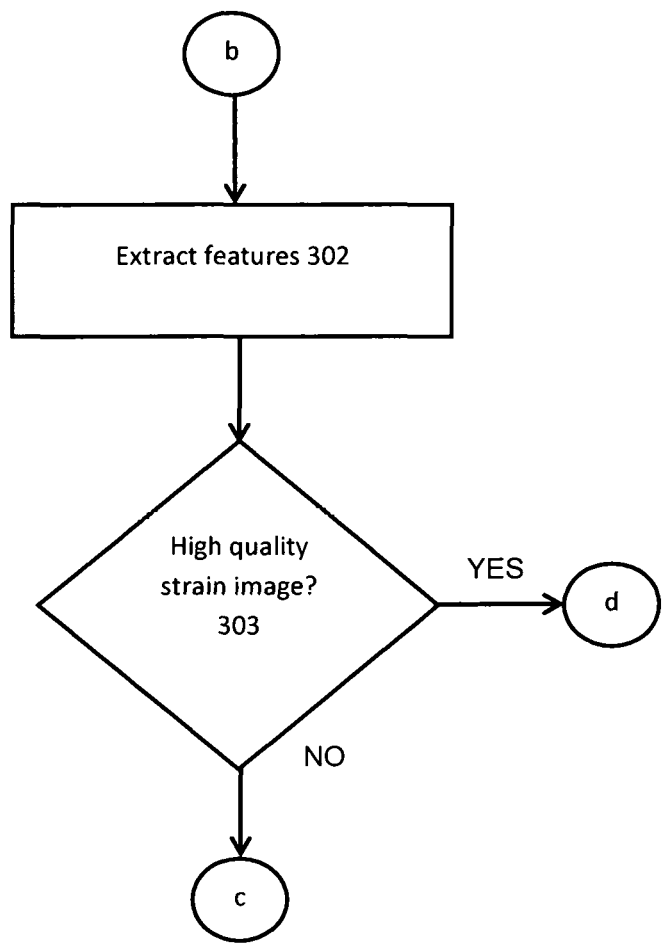
FIG. 3 is an illustration for the feature extraction and frame selection part in the algorithm.
Figure 4:
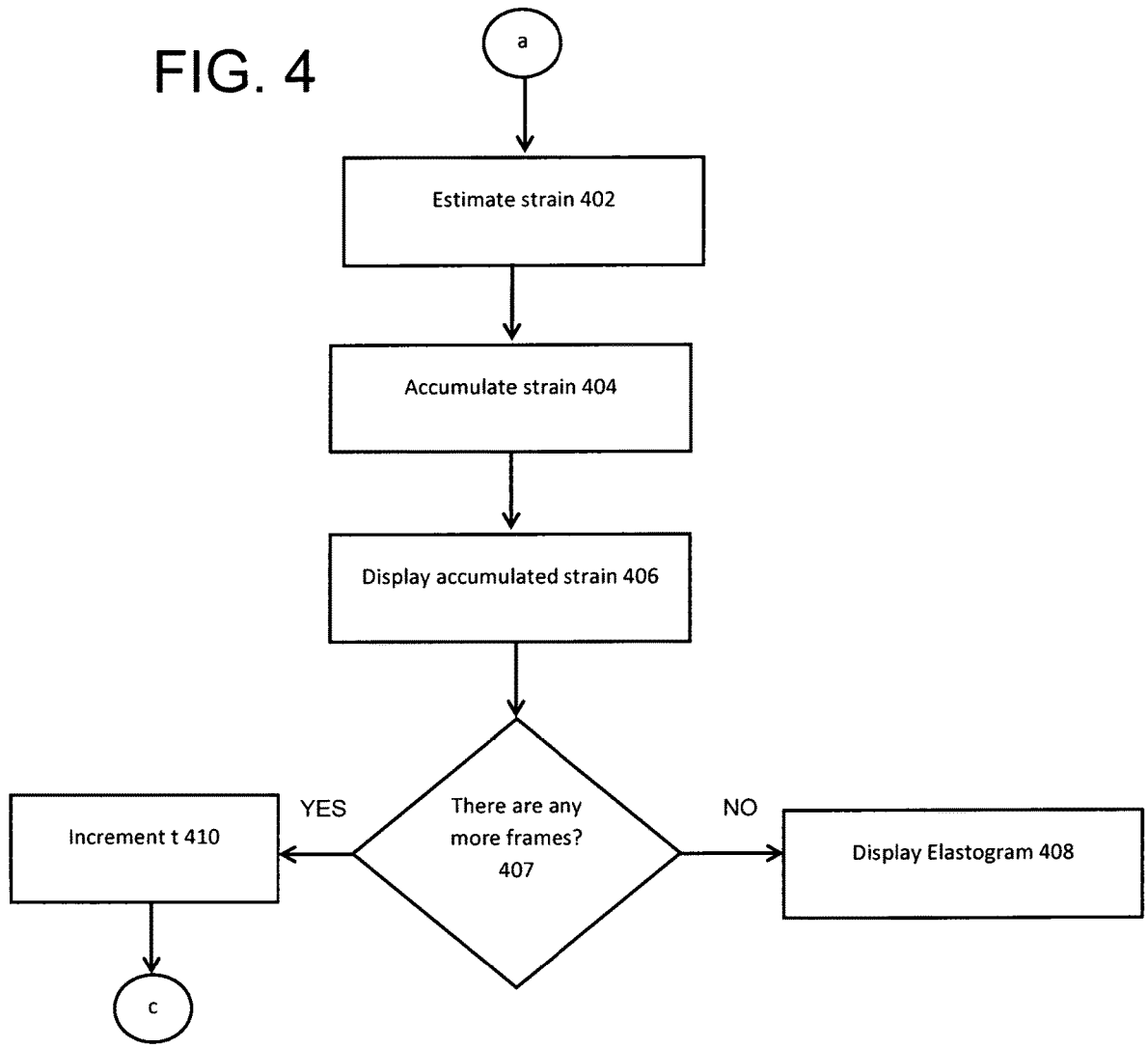
FIG. 4 is an illustration for last part of the algorithm where elastogram is generated.

FIG. 2 refers to the first part of the displacement estimation algorithm where ultrasound images, cine-loop, or videos the region of interest (ROI) is automatically segmented at which there are imaging data (scan lines) acquired by the transducer. In the first block (202) the imaging depth is entered or determined automatically for processing successive or selected frames (204) acquired after time t. Template and search window size (206) are determined automatically by taking a ratio from the imaging frame size (such as 10-20% for 1st HR and 5-10% for the 2nd FIR) and or it can be adjusted manually by the user and also it's considered to not violate the minimum size of template based on speckle size and this is why we all user interfere. The template window is a vector of length equals to 2 or 3 elements and determines the template window size as well as the levels of the hierarchy used. Overlap percentage between template windows is determined to enhance the spectral resolution of the estimated displacement field between chosen imaging frames. There are two objective functions that can be used for the block matching. These functions are computationally efficient and/or accurate including first the Zero-mean normalized cross correlation (ZMCC)

$$R(\Delta x, \Delta y) = \frac{\sum_{x=\frac{tx}{2}}^{\frac{tx}{2}-1} \sum_{y=\frac{-ty}{2}}^{\frac{ty}{2}-1} (f(x+\Delta x, y+\Delta y) - \bar{f}) \times (g(x,y) - \bar{g})}{\sqrt{\left(\sum_{x=\frac{tx}{2}}^{\frac{tx}{2}-1} \sum_{y=\frac{-ty}{2}}^{\frac{ty}{2}-1} f(x+\Delta x, y+\Delta y) - \bar{f}\right) \times \left(\sum_{x=\frac{tx}{2}}^{\frac{tx}{2}-1} \sum_{y=\frac{-ty}{2}}^{\frac{ty}{2}-1} (g(x,y) - \bar{g})\right)^2}} \quad (1)$$

where (x, y) is point of interest, f is the template area around the point of interest in the reference frame at t, g is the search area around the point of interest in the compressed frame at t+1, $\bar{g}$ is the mean of the search window, $\bar{f}$ is the mean of the template window, ty and tx are the axial and lateral template window size, respectively. The second function is the sum of absolute difference (SAD)

$$R(\Delta x, \Delta y) = \sum_{x=\frac{tx}{2}}^{\frac{tx}{2}-1} \sum_{y=\frac{-ty}{2}}^{\frac{ty}{2}-1} |f(x+\Delta x, y+\Delta y) - g(x,y)| \quad (2)$$

Enhanced Hierarchy displacement estimator

The frame selection described in block 204 is trivial such as frame t and t+1. However, the selection of frames used in elastography calculations depends on the frame rate used while acquiring the B-mode ultrasound images and the compression rate done by the user's hand. Frames are included in Elastography calculations whenever the strain between them is within a valid range to show a high quality Elastogram, i.e. if the average strain between two successive frames (t and t+1) is outside this range, frame t+1 is excluded and will be replace by t+2. If the strain between frame t and t+2 is between that range, frame t+2 will be included, and will be excluded otherwise, and so on. This technique assumes a maximum compression of 3% axial strain is applied with typically 1 Hz compression-relaxation cycles as example illustrated in [1], also skilled in the art can expand or shrink the range according to the requirements. The first run of the algorithm is reserved for determining the frame skipping rate and this is done by considering the average displacement and average strain between every 2 successive frames i.e. t & t+1 and then determine the skipping factor that is based on axial displacement and strain between frames to ensure us having a pure axial motion with efficient strain and this is what takes place in block 212.

The size and location of searching window relative to the template window have critical roles in determining the speed and accuracy of the algorithm and that is where we apply our constrains (axial, lateral, and hierarchical). At the $1^{st}$ iteration of the hierarchical model (level 1) we choose search window size so that $$sx = tx + \text{offset}x$$

$$sy = ty + \text{offset}y \quad (3)$$

where sx is the lateral dimension of the search window, sy is the axial dimension of the search window, tx is the lateral dimension of the template window, and ty is the axial dimension of the template window, offset x and offset y are chosen to form the search area. For example, these offsets can be 22 pixels in the axial direction and 12 pixels in the lateral direction assuming and with a displacement greater than 11 pixels in the axial direction and 6 pixels in the lateral dimension, we will get a bad quality strain image This has speed up our algorithm since at the $1^{st}$ level of the hierarchy we usually choose a larger template window and it is frequent to choose the search window≈1.5~2 of the template window and this is computationally expensive specially for a large template window size.

Estimating the displacement field between two frames is performed using block matching techniques. As mentioned before, we can use mainly 2 equation (SAD & ZMCC). SAD is a fast and accurate function that we usually use for block matching so most of results are recorded using SAD function. In another embodiment, ZMCC can be used. In order to improve the processing speed and render a high quality axial strain image at almost real time processing, we adopt a smart algorithm to optimize the trade off between accuracy and speed for estimating high quality axial strain images. The 3 constrains (axial, lateral and hierarchical) are included in the hierarchy recursive (HR) speckle tracking. Axial and lateral constrains have been used before [2] but on estimating axial strain image using RF data not B-mode gray scale ultrasound images like this application. Here we are introducing a hybrid or merged technique involving the power of HR in estimating an accurate and high resolution displacement image along the high computational power added with the axial and lateral constrains based on our application. In one embodiment, we have observed that the 2nd levels of HR tracking lead to a high quality strain image at a reasonable time. At first level we may choose a large template window enough to divide our reference frame (pre-compression) into 10~15 overlapping template windows at most, then we start to search for these template windows inside the second frame (post-compression) in a search window with the criteria discussed and we search row by row. After finishing the $1^{st}$ row, we apply the lateral constrain by assuming that compression is mostly axial so the motion in the lateral direction is just due to poisson effect as described in equation (4).

$$\varepsilon_{lateral} = -\gamma \varepsilon_{axial} \quad (4)$$

This lateral strain is due to very small displacements, so we just determine the displacement of the pixel from the above row as pixel (x,y) and the point in the next row is (x,y+1) and let us assume that point (x,y) moved with displacement (dx,dy) where dx is the lateral displacement and dy is the axial displacement. Then by applying the lateral constrain on the searching window, the search window in the second frame will be centered at (x+dx,y+1+dy)

with size equals to x+4 pixels the template window lateral size, so that it allows only searching x+2 pixels to the right and x+2 pixels to the left. Extending this criteria to the axial constrain, the search window will be equal to the template window axial size x+5, and here it starts to examine if this is a compression cycle or relaxation cycle (motion is upward or downward) and we search only in the direction of motion. Applying these 2 constrains has minimized the required computations as below $$k=m-n+1 \quad (5)$$

where k is the number of operations, m the size of searching window, and n the size of template window. Using equation (5), if a template window size of 32×32 is used along with a search window size with just 1.5 of template window size (48×48),then we have k=17 axial operations and 17 lateral operations with total 289 operations for each tracking point. After applying axial and lateral displacement constrains for the same example we have template window with 32×32 and search window with 36×37, so we will have a total of 20 operations for each tracking point, i.e. the computational complexity reduced with about 14 times than the exhaustive search. After estimating the displacement of each row, we apply a 2D median filter to smooth and avoid any spurious displacement vectors.

After finishing the first level of enhanced HR tracking, displacement estimations between two frames will be obtained with high SNR and low resolution. This displacement field will be used to decide whether these frames underwent enough and valid compression to cause good contrast between tissues or not and that is done by extracting many features that have been studied and reported [4]-[6] besides what we have assumed based on Poission ratio that the later displacement should be symmetric around the axis of the axial compressions and others based on our observation like the entropy of the axial displacement and it's relation with the computed axial strain. To demonstrate that some features may affect the quality of the axial strain image and also features that we have found usefull according to what we have observed from WEKA. To take such decision, we have built a database containing many elastography videos that have been acquired using ultrasound breast phantom (Model 059, CIRS Inc., Norfolk, Va.) and many ultrasound machines of different manufacturers including, and not limited to, IBE, Siemens, Samsung, Philips, GE, Toshiba, Mindray, and Ultrasonix and then we have applied our algorithm over all frames with frame skipping factor equals one i.e. frames to be processed are at t & t+1 and selected good frames (qualitatively) manually (good frames are frames that produce high quality strain image) to extract features and then we have built a data set containing good and bad frames to start feature selection using information gain algorithm included in WEKA. After selecting frames we have trained many classifier with different number of features to see how accurate we can classify good frames from bad frames, we have used KNN, SVM, Naïve bayes that are already implemented in WEKA.

For the second HR level, we apply procedures similar to the first level but with some hierarchy constrains. There is no need to estimate all the first row as we have done in the first level using exhaustive search, because we already know a priori info about its displacement field. We have a higher resolution 2nd level grid to track. First we obtain an initial estimate for the displacement at each point of interest in the $1^{st}$ row of the new grid using the estimated displacement field of level 1 HR, and then the searching area is shifted with a step equals to estimated displacement. The size of this searching area becomes smaller than the one used in the first HR level and we use the small offset used in the axial and lateral constrains based on our calculations of the different displacements and strains from the $1^{st}$ HR level that's implicitly a characteristic feature for the person applying this compression. For the subpixel accuracy in both levels, skilled in the art can use any algorithm based on his accuracy and computation speed requirements, we have used 3 point gaussian fit but still there are plenty of ways like 4-point gaussian estimator, interpolating the original images, center of mass, etc. Also, in addition to our constraints that avoids false peaks in the correlation field, we have used multi-correlation validation technique that is based on applying correlation equation several times on the same searching area but with little shifted or resized template window and multiply all correlation field with each others considering the difference between the template windows location and this can provide us with a correlation field with suppressed noise and amplitude true peak compared with other correlation fields.

After the second HR level is completed, a high resolution and accurate displacement field is reconstructed which can be used directly to estimate a high quality strain image. In one embodiment, we have used different techniques for strain estimation including the least-Square method [7], Savitzky-Golay filter [8], direct displacement gradient. All strain estimation techniques have produced good results since it depends mainly on the quality of the displacement estimation (strain is the gradient of the displacement).

Accumulation of axial strain to produce a higher quality image and increase the SNR. Accumulation depends mainly on the way we are computing strain if it is a lagrange strain then its characterized by higher contrast to noise ratio (CNR) at accumulation and if an Euler strain then its characterized by higher SNR that depends mainly on either we are tracking an object or a pixel. Last step, and this is also based on the physical assumptions that allow us to enhance our results, is applying adaptive normalization to the resulting strain image at which we move with a very wide window that normalize all tissue on the same horizontal level and this is to avoid stress leakage with the depth, since this would lead us to fake decisions thinking that there are hard tissue at high depth.

Also to be stated that the $2^{nd}$ Hierarchical level can totally different than the first one according to matching equation (ZMCC, SAD, SSD), also it can be different algorithm/technique such as using optical flow for the $2^{nd}$ Hierarchical level or using different different form or data to be tracked (register pre-compression image using the estimated displacement field). Also, we can use more number of Hierarchical level and do at each level something different than the previous one, with considering the results estimated from the previous one to enhance and speed up the estimation in the current level and so on until maximum accuracy is achieved at the last level of hierarchy.

While the present invention has been described in terms of particular embodiments and applications, in both summarized and detailed forms, it is not intended that these descriptions in any way limit its scope to any such embodiments and applications, and it will be understood that many substitutions, changes and variations in the described embodiments, applications and details of the method and system illustrated herein and of their operation can be made by those skilled in the art without departing from the spirit of this invention. Rather, the scope of the invention is defined by the following claims. We therefore claim as our invention all that comes within the scope and spirit of these claims.

We claim:

1. A method for reconstructing displacement and strain maps of a target area of a body organ to which a mechanical deformation is applied, comprising:
   receiving, at a processing unit, images depicting tissues of the body organ while the deformation is applied on the target area;
   measuring, with the processing unit, axial and lateral displacements and one or more of axial, lateral, and shear strains of the tissues due to the mechanical deformation using a hierarchy recursive displacement tracking (HR-DT) algorithm, wherein the step of measuring using the HR-DT algorithm includes:
      estimating displacement fields between image frames among the plurality of images at a first resolution level having a course resolution,
      selecting a set of multiple image frames from among the plurality of images as a function of the estimated displacement and prescribed frame selection criteria, and
      for at least the set of image frames, measuring the displacement fields between successive image frames among the set at a second resolution level having a higher resolution than the first level and as a function of the estimated displacement fields;
   differentiating, with the processing unit, between tissues having different stiffness and strain responses based on the measured displacements and strains; and
   generating, with the processing unit, a strain image differentiating tissues of different stiffness and strain responses.

2. The method of claim 1, wherein the deformation applied is varied by at least 0.5%.

3. The method of claim 1, wherein input images are one or more of: original raw RF data, B mode images, cine-loop and videos and raw images received from an ultrasound scanner over a communication interface.

4. The method of claim 1, further comprising:
   applying the mechanical deformation to the target area.

5. The method of claim 4, wherein the applied deformation is a thermal stimulus applied to the target area, and wherein the thermal stimulus comprises changing the temperature of the target area.

6. The method of claim 4, wherein the mechanical deformation is applied by a transducer coupled to an ultrasound scanner.

7. The method of claim 1, wherein the images are captured using one of nuclear medicine cameras, optical cameras, x-ray based imaging, and magnetic resonance imaging.

8. The method of claim 1, wherein the displacement tracking is performed at multiple levels of resolution including a first level having a course resolution and a second level having a higher resolution; and
   selecting a second set of image frames among the first set of image frames in the second higher resolution level, wherein the selection of the second set of images is performed as a function of measured strain values and poisons' ratio and to filter motion artifacts and out-of-plan motion.

9. The method of claim 1, wherein the measuring step comprises:
   selecting the image frames among the plurality of images at the first level having the course resolution
   estimating displacement fields between the image frames among the plurality of images at the first level; and
   for at least a set of image frames, measuring the displacement fields between successive image frames among the set at a second level having a higher resolution than the first level and as a function of the estimated displacement fields.

10. The method of claim 9, wherein estimating displacement fields at the first level is performed using relatively larger search windows thereby producing a coarse estimation of the displacement fields suitable for producing coarse strain images, and wherein measuring the displacement fields at the second level is performed using smaller search windows whereby the displacement fields are measured at a finer resolution and suitable for producing a higher resolution strain image.

11. The method of claim 9 wherein the estimating and measuring of the displacement fields at the first and second levels is performed using hierarchical constraints and axial and lateral continuity constraints.

12. The method of claim 9, further comprising:
   calculating one or more of an axial, lateral and shear strain, wherein strain is calculated as the spatial gradient of the measured displacement.

13. The method of claim 9, wherein the measuring step includes:
   selecting the set of multiple image frames from among the plurality of images as a function of the estimated displacement and prescribed frame selection criteria.

14. The method of claim 9, further comprising:
   reconstructing a high-resolution displacement field map based on the displacement fields measured for a plurality of successive image frames in the set.

15. A system for reconstructing displacement and strain maps of a target area of a body organ to which a mechanical deformation is applied, the system comprising:
   a stimulating device configured to apply a mechanical deformation to a target area of a body organ in a subject;
   an imaging device configured to capture images of tissues of the target area while the deformation is applied to the target area;
   a processing unit connected to the imaging device, wherein the processing unit is configured to receive the images and, based on the images, measure axial and lateral displacements and axial, lateral, and shear strains of the tissues due to the mechanical deformation using a hierarchy recursive displacement tracking (HR-DT) algorithm by:
      estimating displacement fields between image frames among the plurality of images at a first resolution level having a course resolution,
      selecting a set of multiple image frames from among the plurality of images as a function of the estimated displacement and prescribed frame selection criteria, and
      for at least the set of image frames, measuring the displacement fields between successive image frames among the set at a second resolution level having a higher resolution than the first level and as a function of the estimated displacement fields;
   wherein the processing unit is further configured to, based on the measured displacements and strains, differentiate between tissues having different stiffness and strain responses; and
   wherein the processing device is further configured to generate, based on the measured displacements and strains, a strain image differentially depicting tissues of different stiffness and strain responses.

16. The system in claim 15, wherein the imaging device is an ultrasound imaging device and the images are captured using an ultrasound scanner.

17. The system in claim 15, wherein the images are one or more of: original raw RF data, B-mode images, and cine-loop and videos.

18. The system of claim 15, wherein the deformation comprises a mechanical deformation that is repeatedly applied and wherein the applied deformation is varied by at least 0.5%.

19. The system of claim 15, wherein the stimulating device is configured to apply a thermal stimulus to the target area by changing the temperature of the target area and thereby applying the mechanical deformation.

20. The system of claim 15, further comprising: a display device and wherein the processing unit is configured to output the generated strain image via the display device.

21. A method for reconstructing displacement and strain maps of a target area of a body organ to which a mechanical deformation is applied, comprising:
receiving, at a processing unit, images depicting tissues of the body organ while the deformation is applied on the target area;
measuring, with the processing unit, axial and lateral displacements and one or more of axial, lateral, and shear strains of the tissues due to the mechanical deformation using a hierarchy recursive displacement tracking (HR-DT) algorithm;
differentiating, with the processing unit, between tissues having different stiffness and strain responses based on the measured displacements;
generating, with the processing unit, a strain image differentiating tissues of different stiffness and strain responses; and
wherein the step of measuring using the HR-DT algorithm comprises:
estimating displacement fields between image frames among the plurality of images at a first level having a course resolution,
selecting a set of multiple image frames from among the plurality of images as a function of the estimated displacement and prescribed frame selection criteria, and
for at least the set of image frames, measuring the displacement fields between successive image frames among the set at a second level having a higher resolution than the first level and as a function of the estimated displacement fields;
wherein the step of measuring using the HR-DT algorithm further comprises:
identifying a point of interest within a first image frame;
searching for the same point of interest within a subsequent image frame; and
wherein the selecting step includes:
performing the step of estimating the displacement field between the first frame and the subsequent frame at the first level, and
selecting the subsequent frame for inclusion in the set of image frames as a function of the estimated displacement field and prescribed frame selection criteria.

22. The method of claim 21, wherein the prescribed frame selection criteria is a classifier trained to determine whether the subsequent frame includes features suitable for generating a strain image having a sufficient quality.

* * * * *